(12) United States Patent
Kreisel et al.

(10) Patent No.: US 9,278,097 B2
(45) Date of Patent: Mar. 8, 2016

(54) PROPHYLAXIS AND/OR TREATMENT OF PORTAL HYPERTENSION

(75) Inventors: Wolfgang Kreisel, Freiburg (DE); Peter Deibert, Freiburg (DE)

(73) Assignee: Universitatsklinikum Freiburg, Freiburg (DE)

(*) Notice: Subject to any disclaimer, the term of this patent is extended or adjusted under 35 U.S.C. 154(b) by 1284 days.

(21) Appl. No.: 10/559,694

(22) PCT Filed: Jun. 3, 2004

(86) PCT No.: PCT/EP2004/006014
§ 371 (c)(1),
(2), (4) Date: May 1, 2006

(87) PCT Pub. No.: WO2004/108062
PCT Pub. Date: Dec. 16, 2004

(65) Prior Publication Data
US 2007/0004744 A1    Jan. 4, 2007

(30) Foreign Application Priority Data
Jun. 6, 2003  (DE) ................................. 103 25 813

(51) Int. Cl.
  *A61K 31/4985*  (2006.01)
  *A61K 31/00*    (2006.01)
  *A61K 31/519*   (2006.01)
  *A61K 38/31*    (2006.01)
  *A61K 45/06*    (2006.01)

(52) U.S. Cl.
  CPC .............. *A61K 31/4985* (2013.01); *A61K 31/00* (2013.01); *A61K 31/519* (2013.01); *A61K 38/31* (2013.01); *A61K 45/06* (2013.01)

(58) Field of Classification Search
  CPC .................... A61K 31/4985; A61K 31/519
  See application file for complete search history.

(56) References Cited

U.S. PATENT DOCUMENTS

| | | | |
|---|---|---|---|
| 5,973,011 A * | 10/1999 | Noack et al. | 514/742 |
| 6,338,862 B1 * | 1/2002 | Niazi | 424/728 |
| 6,476,037 B1 | 11/2002 | Wallace | |
| 2002/0028764 A1 * | 3/2002 | Grofte et al. | 514/2 |
| 2002/0094988 A1 | 7/2002 | Hines et al. | |
| 2002/0103117 A1 | 8/2002 | Knoell | |
| 2004/0077664 A1 | 4/2004 | Eggenweiler et al. | |
| 2004/0102502 A1 | 5/2004 | Watanabe et al. | |
| 2004/0209908 A1 | 10/2004 | Poitout et al. | |

FOREIGN PATENT DOCUMENTS

| | | |
|---|---|---|
| CA | 2296224 | 1/2000 |
| DE | 199 61 302 | 6/2001 |
| EP | 1 097 711 | 5/2001 |
| EP | 1 129 706 | 9/2001 |
| JP | 03-279326 | 12/1991 |
| JP | 2002-201128 | 7/2002 |
| JP | 2003-518011 | 6/2003 |
| WO | WO-94-28902 | 12/1994 |
| WO | WO-00/43012 | 7/2000 |
| WO | WO-00/54774 | 9/2000 |
| WO | WO-01/56590 | 8/2001 |
| WO | WO-02/19213 | 3/2002 |
| WO | WO 02/060422 A2 * | 8/2002 ............. A61K 31/00 |
| WO | WO-02/060449 | 8/2002 |
| WO | WO-02/062343 | 8/2002 |
| WO | WO-02/100888 | 12/2002 |
| WO | WO-03/022262 | 3/2003 |

OTHER PUBLICATIONS de Franchis et al 'Natural history of portal hypertensino in patients with cirrhosis' Clinics in Liver Disease, 5(3), p. 645-663, 2001. (Abstract only).*
Michelakis et al 'Oral Sildenafil Is an Effective and Specific Pulmonary Vasodilator in Patients with Pulmonary Arterial Hypertension' Circulation, vol. 105, p. 2398-2403, 2002.*
McGoon et al 'Acute and Short-Term Hemodynamic and Clinical Effect of Sildenafil in Pulmonary Arterial Hypertension' The Journal of Heart and Lung Transplantation, 22(1S), p. S153, Jan. 2003.*
G. Jackson, et al., "Effects of Sildenafil Citrate on Human Hemodynamics", *The American Journal of Cardiology*, vol. 83(5A), Mar. 4, 1999, pp. 13C-20C.
M. Rossle, et al., Portale Hypertension, in "Hepatologie," 1995, pp. 271-287.
G. Garcia-Tsao, "Portal Hypertension", *Current Opinion in Gastroenterology*, 2003, pp. 250-258.
R. Wiest, et al., "The Paradox of Nitric Oxide in Cirrhosis and Portal Hypertension: Too Much, Not Enough", *Hepatology*, vol. 35, No. 2, 2002, pp. 478-491.
T. D. Boyer, "Pharmacologic Treatment of Portal Hypertension: Past, Present, and Future", *Hepatology*, vol. 34, No. 4, 2001, pp. 834-839.
H. C. Herrmann, et al., "Hemodynamic Effects of Sildenafil in Men with Severe Coronary Artery Disease", *The New England Journal of Medicine*, vol. 342, No. 22, 2000, pp. 1622-1626.
R. M. Zusman, et al., "Overall Cardiovascular Profile of Sildenafil Citrate", *The American Journal of Cardiology*, vol. 83(5A), 1999, pp. 35C-44C.
U. Gresser, et al., "Erectile Dysfunction: Comparison of Efficacy and Side Effects of the PDE-5 Inhibitors Sildenafil, Vardenafil and Tadalafil Review of the Literature", *European Journal of Medical Research*, vol. 7, 2002, pp. 435-446.
D. T. Manallack, et al., "The Next Generation of Phosphodiesterase Inhibitors: Structural Clues to Ligand and Substrate Selectivity of Phosphodiesterases", *Journal of Medicinal Chemistry*, vol. 48. No. 10, 2005, pp. 3449-3462.
Y. H. Jeon, et al., "Phosphodiesterase: overview of protein structures, potential therapeutic applications and recent progress in drug development", *CMLS Cellular and Molecular Life Sciences*, vol. 62, 2005, pp. 1198-1220.

(Continued)

Primary Examiner — Wu-Cheng Winston Shen
Assistant Examiner — Christopher R Stone
(74) Attorney, Agent, or Firm — Locke Lord LLP; Scott D. Wofsy; Nicholas J. DiCeglie, Jr.

(57) ABSTRACT

The invention provides a medication for the prophylaxis and/or therapy against diseases or complications in connection with portal hypertension, particularly against bleeding complications.

8 Claims, 4 Drawing Sheets

(56) References Cited

OTHER PUBLICATIONS

J. D. Corbin, et al., "Molecular Biology and Pharmacology of PDE-5-Inhibitor Therapy for Erectile Dysfunction", *Journal of Andrology*, vol. 24, No. 6 Supplement, Nov./Dec. 2003, pp. S38-S41.

J-P. Tasu, et al., "Hepatic Venous Pressure Gradients Measured by Duplex Ultrasound", *Clinical Radiology*, vol. 57, 2002, pp. 746-752.

K. Haag, et al., "Correlation of Duplex Sonography Findings and Portal Pressure in 375 Patients with Portal Hypertension", *American Journal of Roentgenol*, vol. 172, 1999, pp. 631-635.

Y. Takase, et al., "Cyclic GMP Phosphodiesterase Inhibitors. 1. The Discovery of a Novel Potent Inhibitor, 4-((3,4-(Methylenedioxy)benzyl)amino)-6,7,8-trimethoxyquinazoline", *Journal of Medicinal Chemistry*, vol. 36, No. 24, 1993, pp. 3765-3770.

Y. Takase, et al., "Cyclic GMP Phosphodiesterase Inhibitors. 2. Requirements of 6-Substitution of Quinazoline Derivatives for Potent and Selective Inhibitory Activity", *Journal of Medicinal Chemistry*, vol. 37, No. 13, 1994, pp. 2106-2111.

A. Albillos, et al., "Accuracy of portal and forearm blood flow measurements in the assessment of the portal pressure response to propranolol", *Journal of Hepatology*, vol. 27, 1997, pp. 496-504.

S. Chung, "Advances in Endoscopy—Management of bleeding in the cirrhotic patient", *Journal of Gastroenterology and Hepatology*, vol. 17, 2002, pp. 355-360.

G. McCormack, et al., "A Practical Guide to the Management of Oesophageal Varices", *Drugs*, vol. 57, No. 3. 1999, pp. 327-335.

I. Colle, et al., "Sildenafil in Rats with Cirrhosis and Portal Hypertension: Systemic and Splanchnic Haemodynamic Effects", *Digest. Dis. Week*, 2003, p. A-736.

I. Colle, et al., "Systemic and Splanchnic Hemodynamic Effects of Sildenafil in Rats with Cirrhosis and Portal Hypertension", Hepatology, vol. 36, No. 4, 2002, p. 510A.

N. Garcia, Jr., et al., "Systemic and Portal Hemodynamic Effects of Sildenafil Citrate", *Gastroenterology*, vol. 120, No. 5, p. A378.

H. A. Ghofrani, et al., "Sildenafil zur Therapie der schweren pulmonalen Hypertonie und des beginnenden Rechtsherzversagens", *Pneumologie*, vol. 56, 2002, pp. 665-672.

D. A. Langer, et al., "Nitric oxide and portal hypertension: Interface of vasoreactivity and angiogenesis", *Journal of Hepatology*, vol. 44, 2006, pp. 209-216.

Budhiraja et al., "Portopulmonary Hypertension* A Tale of Two Circulations", Chest, Feb. 2003, 123:2, pp. 562-576.

Nanji et al., "Arginine Reverses Ethanol-Induced Inflammatory and Fibrotic Changes in Liver Despite Continued Ethanol Administration", The Journal of Pharmacology and Experimental Therapeutics, vol. 299, No. 3, pp. 832-839, 2001.

Ji et al., "Effects of sildenafil citrate on hepatic function and regeneration in normal and alcohol-fed rats", Liver International, 2005: 25: 913-919.

Angele et al., "L—Arginine restores the depressed cardiac output and regional perfusion after trauma-hemorrhage", Surgery 1998; 124:394-402.

Sayin et al., "Sildenafil in primary pulmonary hypertension—is there a subset of patients who respond favourably?", Can J Cardiol vol. 18 No. 6 Jun. 2202, pp. 676 678.

Finley, D.S. et al., "Fatal Variceal Rupture After Sildenafil Use: Report of a Case", Current Surgery, vol. 62, No. 1, pp. 55-56 (2005).

Garcia-Tsao, G., "Portal Hypertension", Curr Opin Gastroenterol 22:254-262 (2006).

* cited by examiner

PROPHYLAXIS AND/OR TREATMENT OF PORTAL HYPERTENSION

The invention relates to a new medication for the prophylaxis and/or the therapy for the portal hypertension (high pressure in the portal vein region) as well as for diseases or medical complications being associated therewith.

Portal hypertension (portal vein high pressure, i.e. high pressure in the region of the portal vein) inter alia is a cause for the threatening bleedings from the upper gastrointestinal tract. Mostly, it involves bleeding from "oesophageal varices", i.e. varicose veins which are formed in the oesophagus, because the hepatic blood flow is disturbed and the blood seeks a "detour circulation". Another problematic complication of the portal hypertension are bleedings from fundus varices. Besides, other severe or life-threatening complications of the portal hypertension are known (hepatic encephalopathy, hepatorenal syndrome, hepatopulmonal syndrome, ascites, spontaneous bacterial peritonitis, metabolic disorder following decreased blood flow through the liver.

The acute bleeding complication is treated by medicaments (e.g. Vasopressin and analoga thereof, Somatostatin and analoga thereof, Angiotensin-2-receptor-antagonists) and/or by endoscopic procedures (balloon tamponage, sklerosation, varice banding, injection therapy with acrylic resins, TIPS (transjugular porto-systemic stent-shunt)). The primary or secondary prophylaxis conventionally is carried out by medicaments (non-cardioselective β-blockers; nitrates), endoscopy (sklerotherapy, varice banding, TIPS) or surgery (shunt-operations). Through the prophylaxis by medicaments by means of administration of β-blockers or nitrates, a decrease of the portal vein pressure by means of decreasing heart rate, peripheric vascular resistivity and systemic blood pressure (see literature S. Chung, J. Gastroenterol. Hepatol. 2002, 17:355-360; and G. Mc. Cormack and P. A. Mc. Cormick, Drugs 1999, 57:327-335).

Just when considering the example of nitrates, the dilemma of drugs, which generally act in a vasodilatory manner, is demonstrated, as becomes apparent from G. Garcia-Tsao: "Portal hypertension". Current Opinion in Gastroenterology, 2003, 19, p. 250-258; and R. Wiest and R. J. Groszmann: "The Paradox of Nitric Oxide in Cirrhosis and Portal Hypertension: Too Much, Not Enough", Hepatology 35, No. 2, 2002, pp. 478-491: a decrease of the peripheral vascular resistivity or the systemic blood pressure may even increase the blood congestion towards the liver and therefore may render the pathologic situation even worse. That is, even a speculated general blood circulation increase or vasodilatation, being caused by a medicament, does not automatically mean that the medicament has an effect of increasing the blood flow through the liver and/or has an activity against portal hypertension. The established medicaments such as β-blockers, Vasopressin and its derivatives, Somatostatin and its derivatives decrease portal vein pressure by reducing the arterial flow towards the liver. Thereby, the whole (portal) blood stream to the liver, which is already affected, is, however, worsened even further. Therefore, for many years it has been sought for substances, which decrease the portal vein pressure more or less selectively. In particular, it is desired to enable a therapy, by means of which the portal blood flow to the liver is increased, without decisively changing the arterial perfusion of the liver.

In addition to the problems of the medicamentous therapy, the portal hypertension is a disease state of a very complex and variable etiology and may not be equated with the patho-logic-anatomically defined condition of liver cirrhosis. Different from liver cirrhosis as such, portal hypertension may be a consequence of liver cirrhosis, but also of completely other causes, as outlined in the following list:
(I) Prehepatically:
thromboses in the region of the portal vein
arterio-venous fistula
each disease with a significantly enlarged spleen (increased blood flow towards the liver)
(II) Intrahepatically:
a) Presinusoidal:
schistosomiasis (bilharciosis)
sarkoidosis and other granulamateous diseases
primary biliary cirrhosis (still before it is converted into a real cirrhosis) myeloproliferative syndromes, e.g. chronic myeloic leukemia, osteomyelofibrosis
lymphatic systemic diseases
collagenoses (e.g. systemic lupus erythematodes, sklerodermy)
congenital liver fibrosis liver fibroses of other origins
M. Osler (inherited arterio-venous disorders, inter alia also in the liver) "idiopathic portal hypertension" (PH without clear origin)
b) Sinusoidal.
liver cirrhosis
nodular regenerative hyperplasy
toxic liver damage
hepatitis with severe course
c) Posisinusoidal:
liver cirrhosis
toxic liver damage
veno-occlusive disease (VOD)
nodular regenerative hyperplasy
hepatitis of severe course
(III) Posthepatic:
right-sided heart failure
tricuspidal insufficiency
pericarditis constrictiva
Budd-Chiari syndrome (thromboses of the liver veins)
disorders of the liver veins
compression of the liver veins (e.g. by cancers)

Prior concepts of prophylaxis and therapy against portal hypertension do not have sufficient success ratios. Up to now, neither bleeding complications nor the numerous other diseases or medical complications of a portal hypertension can be treated or prevented satisfactorily.

Therefore, it is an object of the invention to broaden and improve the therapeutic possibilities of the primary and/or secondary prophylaxis, and/or of the therapy of the portal hypertension and of diseases or complications being associated therewith or related thereto.

This object is solved by the use according to the invention as described herein. Further subject-matters of the invention and preferred embodiments of the subject-matters according to the invention are also defined herein.

DETAILED DESCRIPTION OF THE INVENTION

With the present invention, a completely novel biochemical or pharmacological starting point is established, which offers better therapeutic possibilities for the prophylaxis and/or therapy of the portal hypertension and diseases or complications being associated therewith or related thereto.

As a basis for this novel starting point and the improved therapeutic possibilities, it was surprisingly found that inhibitors of phosphodiesterase 5 are capable of decreasing the portal vein pressure significantly, of increasing the portal vein diameter, and of increasing the portal vein flow significantly.

Inhibitors, which are specific towards the phosphodiesterase 5 (PDE-5) (presently, 11 types of phosphodiesterase from humans are known), are known as such, but for indications other than in the present invention, or have been studied in another context.

The best-known indication field is the male erectile disfunction (MED, impotence) (see WO 94/28902 A), and the best-known drug developed for this purpose is the compound Sildenafil (INN) (see review article about this and other PDE 5-inhibitors for this purpose, U. Gresser and C. H. Gleiter in Eur. J. Med. Res. 2002, 435-446). Chinazolines having cGMP-phosphodiesterase-inhibiting activity are, e.g., described in J. Med. Chem. 1993, 36:3765 ff. and in J. Med. Chem. 1994, 37:2106 ff. The WO 02/060449 A describes a pharmaceutical formulation, comprising a PDE 5-inhibitor combined with nitrates (pryzolo[4,3-d]pyrimidines and nitrates or thienopyrimidines and nitrates). The pharmaceutical formulation is described for the preparation of a pharmaceutical, which is alleged to be possible for treatments of a series of various diseases: angina, hypertension, pulmonary hypertension, congestive heart failure (CHF), chronic obstructive pulmonary disease (COPD), cor pulmonale, right-sided heart insufficiency, arteriosclerosis, conditions of decreased passage of heart vessels, peripheral vascular diseases, strike, bronchitis, allergic asthma, chronic asthma, allergic rhinitis, glaucoma, (irritable Bowel-syndrome) irritable intestine syndrome, cancers, renal insufficiency and liver cirrhosis. The WO 02/062343 A2 describes a pharmaceutical formulation, comprising at least a PDE 5-inhibitor and at least an endothelin-receptor antagonist, for the preparation of a medicament which is proposed for the same diseases as in the WO 02/060449 A and further for erectile disfunctions and for the treatment of female sex diseases. EP 1 097 711 A2 describes the use of specific PDE 5-inhibitors, e.g. Sildenafil, for treatment of pulmonary hypertension. H. A. Ghofrani et al. (Pulmologie 56, 665-672 (2002) describe Sildenafil for the treatment of pulmonary hypertension and possibly also for the beginnings of heart insufficiency.

Further, N. Garcia Jr. et al. in Digestive Disease Week 2001, Abstract A-391, as well as I. Colle et al. in Digestive Disease Week 2003, Abstract No. S1553 report in respective abstracts about animal experimental studies on systemic or splanchnic or portal haemodynamic effects of Sildenafil in rats. Highly artificial conditions of the study are chosen by administering this substance i.v. or intraarterially (into the Arteria mesenterica superior) in very high doses (0.1, 1 and 10 mg/kg body weight in Garcia et al., and 0.01-10 mg/kg body weight in Colle et al.). It was observed that the arterial vascular resistivity decreases in a very short-term effect (clearly below 5 minutes); with respect to the portal venous pressure, the indications by Garcia et al. and Colle et al. are contradictory. The artificial animal experiments suggest an unphysiologic, short-term and general, i.e. a non-selective vasodilatory effect of Sildenafil as a consequence of direct intravasal administration to the rat.

The particular effectivity of PDE 5-inhibitors, alone or in combination with other drugs against portal hypertension, especially in combination with substances acting in a lowering manner on the heart rate and alternatively on the arterial blood flow towards the liver, such as β-blockers or Vasopressin, Vasopressin analoga such as Terlipressin, Somatostatin or Somatostatin analoga such as Octreotid, for the primary or secondary prophylaxis and/or for the therapy of portal hypertension, particularly for the treatment of bleeding complications, is, however, neither contemplated in the above-mentioned documents, nor may the hypothetic indications of the mentioned documents suggest the specific results of a significant decrease of the portal vein pressure and a significant increase of the portal vein flow as found according to the present invention. Contrary to the animal experiments of Garcia et al. and Colle et al., qualitatively and quantitatively different effects have been obtained in humans according to the present invention.

The present invention provides the use of PDE 5-inhibitors for the primary or secondary prophylaxis and/or for the therapy against portal hypertension, as well as against disease conditions or risks which are associated with portal hypertension. In particular, these are the following diseases: bleeding complications of the portal hypertension, particularly with bleedings from oesophagus varices, fundus varices and/or in case of portal hypertensive gastropathy; further the diseases of hepato-renal syndrome, hepato-pulmonal syndrome, hepatic encephalopathy, spontaneous bacterial peritonitis and ascites.

Moreover, the use of a PDE 5-inhibitor or of a pharmaceutical composition containing a PDE 5-inhibitor is indicated for the prophylaxis and/or therapy against illnesses or disease conditions, which can be controlled and thereby prevented by a decrease of the portal vein pressure and/or by an increase of the portal vein flow. Therefore, further diseases or disease conditions are contemplated, which can be prevented or alleviated or even healed by the improved blood flow through the liver obtained by the decrease of the portal vein pressure and/or the increase of the portal vein flow. Among these, there are primarily such diseases or disease states which are characterized by disorders of the metabolism or of the blood circulation in connection with the liver, e.g. detoxification disorders, reduced or disturbed decomposition/catabolism of medicaments, wrong substance breakdown, build-up of a detour circulation round the liver, immune- or protection-deficiency, congestion of blood in the spleen and subsequent diseases such as leucocytopeny, thrombocytopeny, disorder in the synthesis of blood clotting factors, disorders of brain functioning, and the like.

The effect of inhibitors of PDE-5 on the increase of portal blood flow can also be utilized in the healthy liver, which may be threatened by endogenous toxic substances or by the consumption of medicaments, drugs and/or alcohol or similar exogenous, particularly toxic substances. When a substance is metabolized in the liver, which is particularly the case for the mentioned exogenously added substances and typically also for other endogenous or exogenous substance types, its metabolism can be specifically influenced by an increase of a blood flow through the liver, which results from the increased flow towards the portal vein without pressure increase of the portal vein itself. The metabolic catabolism of the endogenous or the exogenously added substance in the liver may thus be enhanced.

Corresponding to this concept, the present invention additionally provides a combination-medication or -preparation for influencing the metabolism of a substance, wherein the following is combined, within the same or in separate application forms:

a PDE 5-inhibitor, and
a substance, the metabolism of which shall be influenced, and which is selected from the group consisting of medicaments, drugs or toxic substances such as ethyl alcohol.

Also in this aspect of the invention, influencing the metabolism of the substance involves an increase of the portal vein flow and thereby advantageously an increase of the blood flow through the liver. In the combination with an exogenously added substance, that substance may be administered concurrently with, after, or particularly before the administration of the PDE 5-inhibitor or the pharmaceutical composition containing a PDE 5-inhibitor.

Specifically in case of ascites, a combination of a PDE 5-inhibitor with any diuretic, e.g. Furosemid (an example for a loop diuretic) or spironolacton (an aldosteron antagonist), is particularly suitable in order to enhance the prophylactic or healing effect.

The measurement of the portal vein pressure, the portal vein diameter and the portal vein flow may be carried out with known methods, e.g. non-invasively by means of Doppler sonographic measurements (see e.g. A. Albillos et al., J. Hepatol. 27, 496-504 (1997)), or invasively by determining the hepatovenous pressure gradient (HVPG) (see J. P. Tasu et al., Clin. Radiol. 57, 746-752 (2002)) or of the wedged hepatic vein pressure (WHVP).

As PDE 5-inhibitors, PDE 5-inhibitors known as such from the above-mentioned documents and, due to their particular selectivity for PDE 5 as against other phosphodiesterases, in particular the following substances are suitable for the use according to the invention: Sildenafil (INN), i.e. 1-{[3-(6,7-Dihydro-1-methyl-7-oxo-3-propyl-1H-pyrazolo-[4,3-d]pyrimidin-5-yl)-4-ethoxyphenyl]sulfonyl}-4-methyl-piperazine (citrate), Tadalafil (INN), i.e. (6R,12aR-2-methyl-6-(3, 4-methylendioxyphenyl)-12,12a-dihydro-6H-pyrazino[1,2: 1,2]-pyrido[5,4-b]indol-1,4(2H,3H)-dion, and Vardenafil (structures see U. Gresser and C. H. Gleiter above). These also include the modified and analogous forms of these substances, which are known to the skilled person and which are also attributed an inhibition of PDE 5.

The surprisingly distinct selectivity of the effect on the vessels in humans relevant for the portal hypertension, as observed within the framework of the present invention, appears to be significant for the surprising success of the PDE 5-inhibitors as drugs specifically for the above-described indications: While the vessel resistivity of the arterial vessels supplying the liver remains unchanged or even increases (and, correspondingly, maintaining or decreasing the arterial inflow to the liver), the portal inflow significantly increases. Particularly since the physiologic arterial and portal blood inflow to the liver, respectively, are complementary—i.e. that the arterial blood flow decreases when the portal blood flow inreases, and vice versa—it is assumed that due to this complementarity the selective effect results in the surprising effectivity at the target site.

Since the effects preferably supplement each other, a combination may be advantageously carried out according to the present invention by the use, in a common or in separate formulation(s) (combinatory medication), of the PDE 5-inhibitor in combination with another drug against portal hypertension. The combined drug may be particularly selected from the group of Vasopressin and analogs thereof, such as Terlipressin and Somatostatin as well as their analogs such as Octreotid, in order to contribute to a synergistic increase of the arterial vascular resistivity and thus to a decrease of the arterial blood supply to the intestine and the liver (cf. the physiologic complementarity of the blood flow through the liver). Alternatively, drugs decreasing heart rate, particularly β-blockers, are usable. A combination of the PDE 5-inhibitor with nitrates/organic nitrates, and/or without endothelin receptor antagonists, may be obsolete, depending on the desire and the indication, in order that no reverse effects or risks, especially in the case of nitrates/organic nitrates as described above, may occur.

The PDE 5-inhibitor may be contained as the drug together with a pharmaceutically acceptable carrier and/or diluent(s) and/or additive(s) in formulations suitable for administration to human patients. The drug or the composition may have a solid, semisolid, gelatinous or hydrogel-like, a liquid or a similar consistency and may, for example, be embodied in the form of a liquid, a suspension, a powder, a tablet, a pill, a capsule, a sustained-release dosage form, and the like. The compositions suitably contain a therapeutically effective amount of the PDE 5-inhibitor together with a suitable amount of a carrier or vehicle, in order to provide the form appropriate for the administration for the patient.

Such formulations may, e.g., comprise alone or in combination: suitable pharmaceutical additives such as starch, cellulose and cellulose derivatives, glucose, lactose, sucrose, gelatin, silica gel, magnesium carbonate, magnesium stearate, sodium stearate, glycerol monostearate, talc, sodium chloride, dried skimmed milk, glycerol, propylen, glycol, water, ethanol or another alcohol, and the like; sterile liquids such as water, salt solutions and aqueous dextrose solutions and glycerol solutions, and/or oils, including paraffin oils of animal, plant or synthetic origin such as peanut oil, soya oil, mineral oil, sesame oil, and the like. The administration form may be a typical administration form, for example oral, parenteral, particularly for injection, a transdermal system, nasal or for inhalation. For acute bleedings, in particular intravenous (i.v.) injections of a PDE 5-inhibitor and preferably in combination with a drug decreasing the heart rate or alternatively the arterial blood flow through the liver such as β-blockers, alternatively with Vasopressin or Somatostatin or their derivatives, is contemplated.

For the administration the PDE 5-inhibitor and optionally the mentioned combination therapeutics are suitably present in one of the above-mentioned compositions, formulations or devices, and are contained in an amount effective for humans for the prophylaxis or for therapy of the above-mentioned diseases or disease conditions. For example, a suitable amount, relative to the total amount, respectively is at least 0.0001 wt.-%, normally 0.01 to 20 wt.-%, preferably 0.01 to 10 wt.-%. As the dose, an amount of a drug of at least 0.0001 mg/kg, e.g. in a range of from 0.0001 to 1000 mg/kg, preferably 0.01 to 100 mg/kg and particularly 0.1 to 20 mg/kg body weight of the treated patient is suitable, wherein a single dose is respectively administered, as described locally or systemically, one or several times daily or weekly, in case of depot or slow-release-formulations optionally also at a lower frequency.

It has been observed that the effects of the PDE 5-inhibitor may be different, depending on the administration type and dose. Surprisingly, a particularly selective effect of the PDE 5-inhibitor on the portal hypertension was observed, when the PDE 5-inhibitor or the pharmaceutical composition containing the PDE 5-inhibitor had been administered orally, and particularly in the case, when the dose is low or fairly low, e.g. at a respectively administered dose of the PDE 5-inhibitor of 0.01 to 10 and particularly 0.1 to 1.5 mg PDE 5-inhibitor per kg body weight. For comparison, it is noted that a maximal serum concentration of the PDE 5-inhibitor, as achieved after such an oral administration, is significantly below the serum concentration of this PDE 5-inhibitor, which is achieved by an injection or infusion (i.v., i.a. or i.m.) of the PDE 5-inhibitor with a concentration of 0.01 mg/kg body weight. It may be assumed that the particularly effective activity of the PDE 5-inhibitor, when orally administered at the described dose, is based on a "first pass" effect by the liver. If nevertheless an injection is contemplated as the administration form, the dose concentration should preferably be adjusted at a correspondingly low level, e.g. 0.01 mg/kg body weight. Correspondingly, the dose per administration advantageously lies in a range, in which a selective effect on the target vessels (determinable by e.g. increase of the portal blood flow and a concurrently maintained or increased resistivity (defined as Resistivity Index Ri)) is clearly ensured, e.g. lower than 1.5 (further preferred lower than 1.0) mg/kg body weight in an oral administration, lower than 0.01 (further preferred lower than 0.005) mg/kg body weight in case of injection or inhalation, and lower than 0.005 (further preferred lower than 0.001) mg/kg body weight per minute in case of infusions.

With respect to the combined therapeutics or the exogenously supplied substance, to be decomposed metabolically, of the combination-medication or -preparation according to the present invention, the skilled person may chose, depending on the application case and the demand, those administration forms, administration compositions and amounts which are common for the respectively combined drug or the exogenously supplied substances. Therefore, independent from the PDE 5 administration form, suitable pharmaceutically acceptable carriers, diluents, additives etc., and suitable formulations for the optionally combined drugs of the combination-medication or combination-preparation are contemplated.

The production of a medicament or of a combination medication as well as the medial use for the prophylaxis and/or therapy are readily revealed for the skilled person from the above description.

The significant effectiveness of PDE 5-inhibitors for the specific indication fields mentioned above results from the following:

Portal Hypertension,
Bleeding Complications, etc.:

In a pilot study, partially a significant increase of the diameter of the portal vein and the spleen vein was determined. The maximal flow rate of the blood in the portal vein and in the spleen vein decreased only slightly. The resistivity of the arterial blood flow through the liver showed almost no change, or it even increased. To the contrary, the portal vein flow through the liver significantly increased (partially e.g. by about 30%).

Thus, by the pressure decrease and the enhancement of the flow in the portal vein circulation, the formation of collaterals between the portal vein system and the venous vascular system and thus, the formation of oesophagus varices and/or fundus varices can be prevented, or by means of a decrease of the portal vein pressure by administering inhibitors of PDE 5, the occurrence of bleeding or a recurrence of bleeding can be prevented. Due to the rapid physiologic response and the generation of the effect "decrease of portal vein pressure" instantly or directly after administration of the PDE 5-inhibitors, a therapy of acute bleeding complications is also possible.

Hepato-Renal Syndrome:

This disease represents a worsening of the renal function with a regulatory disorder, although the kidney itself is intact. The conventional therapy, namely volume administration, administration of albumin or of Terlipressin, is not satisfactory.

According to the invention, the blood flow through the liver is increased due to the use of PDE 5-inhibitors, so that it is to be expected that blood from the portal vein is supplied to the systemic circulation, and an improvement of the hepato-renal syndrome is to be expected.

Hepato-Pulmonal Syndrome:

This disease is associated with a portal hypertension and an arterial oxygen subsaturation. Dyspnea and diminishing performance are the symptoms thereof. Hereby, short-circuit connections between the branches of pulmonary arteries and pulmonary veins occur. Therefore, the oxygen-deficient blood is partially not replenished any more with oxygen in the lung.

By means of the decrease of portal vein pressure and thereby the positive effect on the portal hypertension according to the present invention, an improvement of the hepato-pulmonal syndrome is to be expected as well.

Hepatic Encephalopathy:

This disease is a disease condition, also associated with the portal hypertension, with non-inflammatory brain damages or brain disorders. Due to diminished portal blood flow, the blood from the gastrointestinal tract is less detoxified, especially when a collateral circulation is present at the same time. Also in this case, a significant positive effect is expected, since due to a pronounced improvement of the blood flow through the liver, less blood flows around the liver and thereby blood may be detoxified better.

Further Diseases or Disease Conditions, the Situation of which is Improved by the Decrease of Portal Vein Pressure and/or by Increase of Portal Vein Flow:

Correspondingly, there is a range of diseases or disease conditions, which can be prevented or even healed by an improved blood flow through the liver. For, the cause of such diseases is just the distortion of blood flow and the metabolic disorder of the liver, or the formed detour circulation around the liver, which are accompanied in the portal hypertension. Therefore, among these further diseases or disease conditions, there are e.g. detoxification disorders, decreased or disturbed decomposition/catabolism of medicaments, wrong substance breakdown, build-up of a detour circulation around the liver, protection- or immune-deficiency, disorder in the synthesis of blood clotting factors, disorders of the brain functioning, congestion of the blood in the spleen and subsequent diseases such as leucocytopeny, thrombocytopeny, etc.

By decreasing the portal vein pressure and/or by increasing the portal vein flow, the condition of such or similar diseases therefore will be improved expectedly.

Further Combination-Concepts

If the increase of the portal vein flow is advantageously accompanied by an increase of a blood flow through the liver, it is to be expected that also in the normal healthy liver the metabolism of a substance being metabolized in the liver is influenced. Among substances being influenced in their metabolism in this manner, there are endogenous toxic substances and particularly exogenously added substances such as medicaments, drugs or toxic substances such as ethyl alcohol. The negative effects of these substances on the organism thereby may be controlled or eliminated. Furthermore, in a combination-medication of the PDE 5-inhibitor with another therapeutic substance in this manner, it is possible to specifically influence the pharmacokinetic of this combined therapeutic substance.

Such further combination-medications or combination-preparations therefore extend advantageously the therapy concepts of completely other diseases which are respectively associated with the combined therapeutic substance, and independently from the presence or potential danger of portal hypertension.

Ascites and Spontaneous Bacterial Peritonitis:

By decreasing the pressure in the portal vein system, the condition of ascites will be improved expectedly.

The invention will be explained in the following by representative examples by the use of an exemplified PDE 5-inhibitor.

EXAMPLES

1$^{st}$ Series of Examples

With ten volunteers, the base values of the blood flow through the liver were measured in the morning before breakfast by means of common sonographic or Doppler sonographic methods. Subsequently, 100 mg Sildenafil were administered orally for each test person. On the average, 90 minutes after administration of this drug, the measurements were repeated.

The measurement parameters and the results are summarized in the following Table.

The results show a slight decrease of the arterial blood pressure and a significant increase of the diameter of the portal vein and the spleen vein. The maximal flow rates of the blood in the portal vein or the spleen vein practically did not decrease, and also the values for the resistivity of the arterial vessels Arteria hepatica communis and Truncus coeliacus hardly changed. To the contrary, the inflow of the blood in the portal vein increased by 32.5%. From this, a decrease of pressure in the portal vein can be concluded from the administration of an effective amount of a representative phosphodiesterase 5-inhibitor.

TABLE

| Measurement parameter (unit) | MW | SD | Change by Sildenafil (absolute) | Change by Sildenafil (in %) |
|---|---|---|---|---|
| Systolic blood pressure (mm Hg) | 122 | 10.5 | −12.21 | −10.0 |
| Diastolic blood pressure (mm Hg) | 80.5 | 5.5 | −7.64 | −9.5 |
| Diameter of portal vein (mm) | 11.7 | 0.9 | 1.5 | +12.8 |
| Vmax of portal vein (cm/sec) | 30.5 | 7.9 | −1.63 | −5.3 |
| Diameter of V. lienalis (mm) | 7.7 | 0.7 | 1.0 | +13 |
| Vmax of V. lienalis (cm/sec) | 20.14 | 4.4 | −0.47 | −2.3 |
| Resistivity Index of A. hepatica communis | 0.67 | 0.07 | +0.03 | +4.48 |
| Resistivity Index of Truncus coeliacus | 0.75 | 0.05 | −0.115 | −1.5 |
| Portal vein flow (l/mm) | 0.83 | 0.22 | +0.27 | +32.5 |

MV: mean value
SD: standard deviation
Vmax: maximal flow velocity
n = 10 (in case of portal vein flow n = 5)

2$^{nd}$ Series of Examples

In a further study, 16 healthy volunteers and 15 patients having portal hypertension (origin: liver cirrhosis in the status of Child A) were subjected to the following treatment:

In both the volunteers and the patients with empty stomach (10 hours of food leave), firstly the pulse rate and blood pressure under lying condition and subsequently the parameters of liver haemodynamics were measured by Doppler sonography.

Doppler Sonography:

The portal vein pressure is derived from the values obtained from the application of the apparatus Elegra from Siemens having a 3.5 MHz sectorial scanner (K. Haag et al., Am. J. Roentgenol 1999; 172: 631-635). Each measurement was carried out three times in total. The mean value from all three measurements was used. The measurements were carried out in the resting expiratory position. When measuring the flows and the flow volumina, the sonic angle lied below 60°. The sectional plane was basically chosen such that the vessel will be illustrated in its longitudinal route.

The following measurement points and measurements were set:

Vena Portae:

Illustration in the route of the Ligamentum hepatoduodenale, in the sectional plane from Confluens venosum up to the division into the right and the left portal vein main stem.

Caliber measurement in the Vena portae.

Flow measurements in the Vena portae as well as in their intrahepatic main stems. The determination of the flow volume in the portal vein, the Vena lienalis and the Vena mesenterica was carried out by Doppler-sonography, as measured by the options of the apparatus and by calculation through the formula:

$$\text{flow} = \pi \cdot d^2/4 \cdot V_{max} \cdot 2 \cdot 60, \text{ wherein d is indicated in cm and } V_{max} \text{ is indicated in cm/s.}$$

Vena Lienalis:

Sectional illustration in the medium upper stomach, measurement of caliber and flow.

Vena Mesenterica Superior:

Illustration along its route from Confluens venosum, measurement of caliber and flow.

Truncus Coeliacus, Arteria Lienalis, Arteria Hepatica Communis:

Sectional illustration in the medium upper stomach, measurement a few centimeters below the furcation, determination of the Pourcelot Index ($Ri = (V_{max[sys]} - V_{max[diast]})/V_{max[sys]}$).

In the Arteria hepatica communis, particularly the flow direction was documented, for excluding a relevant stenosis of the Truncus (here, a turn of flow would occur).

Administration of the Medicament:

Each volunteer obtained 10 mg Vardenafil orally. After one hour, the blood pressure and the pulse rate in lying condition were measured, 10 ml serum were withdrawn for the level control of Vardenafil, and a new measurement of the liver haemodynamics was carried out by Doppler-sonography (as in the case of the above-mentioned initial measurement).

A final examination for measuring the liver haemodynamics after the lapse of the effect of Vardenafil was carried out after latency of at least 24 hours after medicament administration.

Figure 1:
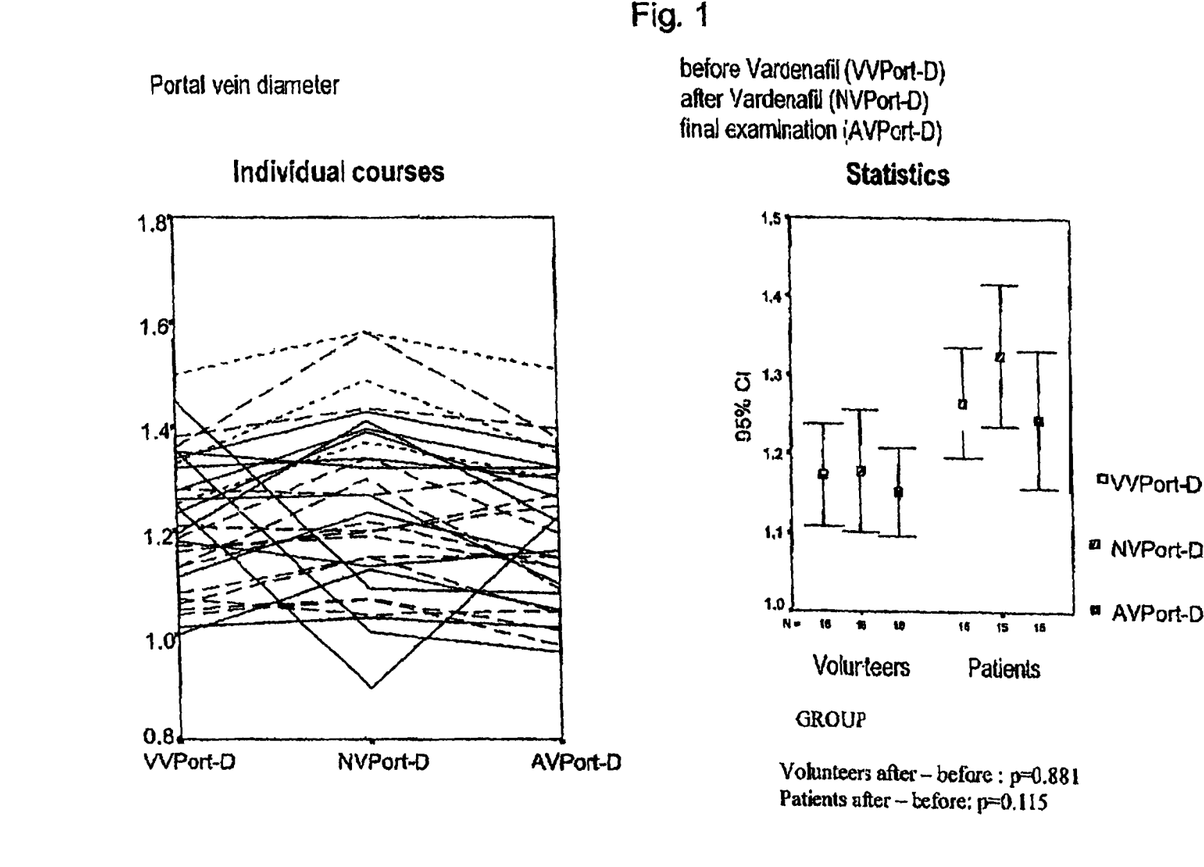
FIG. 1 shows the measurements of portal vein diameter in patients before (V), 1 h after oral administration (N) and in the final examination (A).
Figure 2:
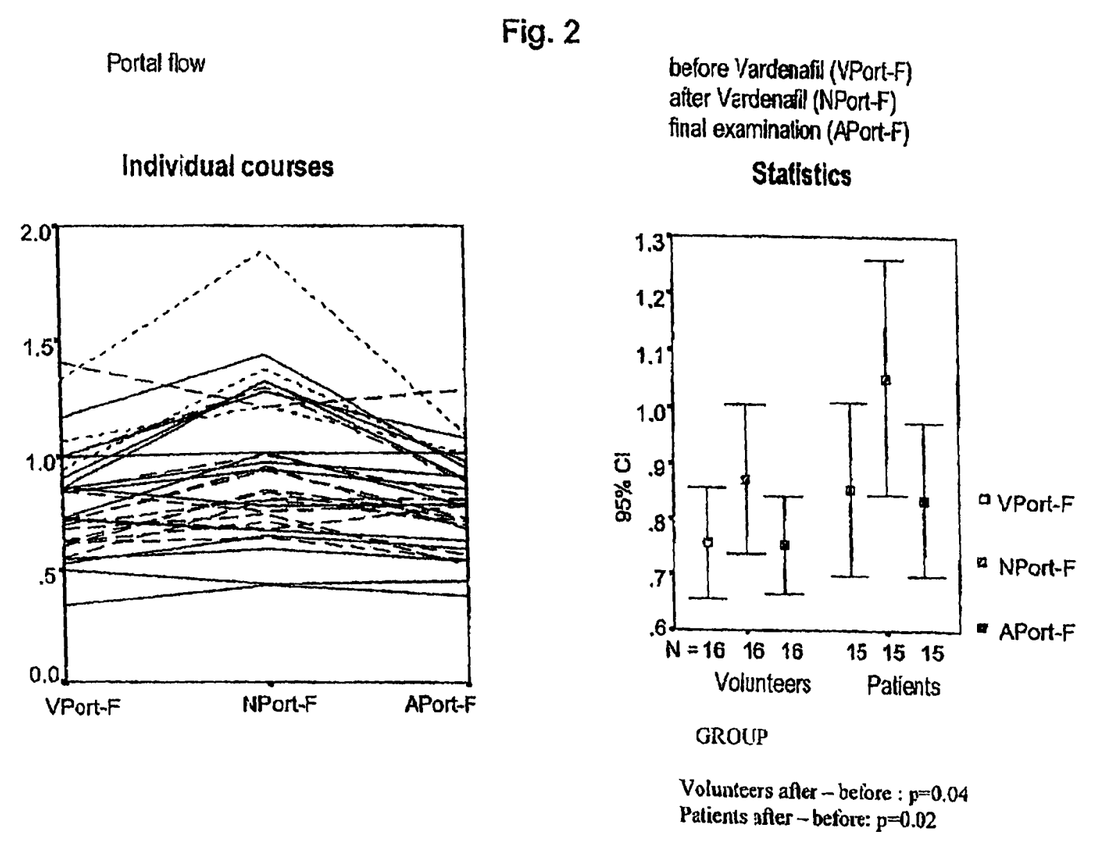
FIG. 2 shows the measurements of portal flow in patients before (V), 1 h after oral administration (N) and in the final examination (A).
Figure 3:
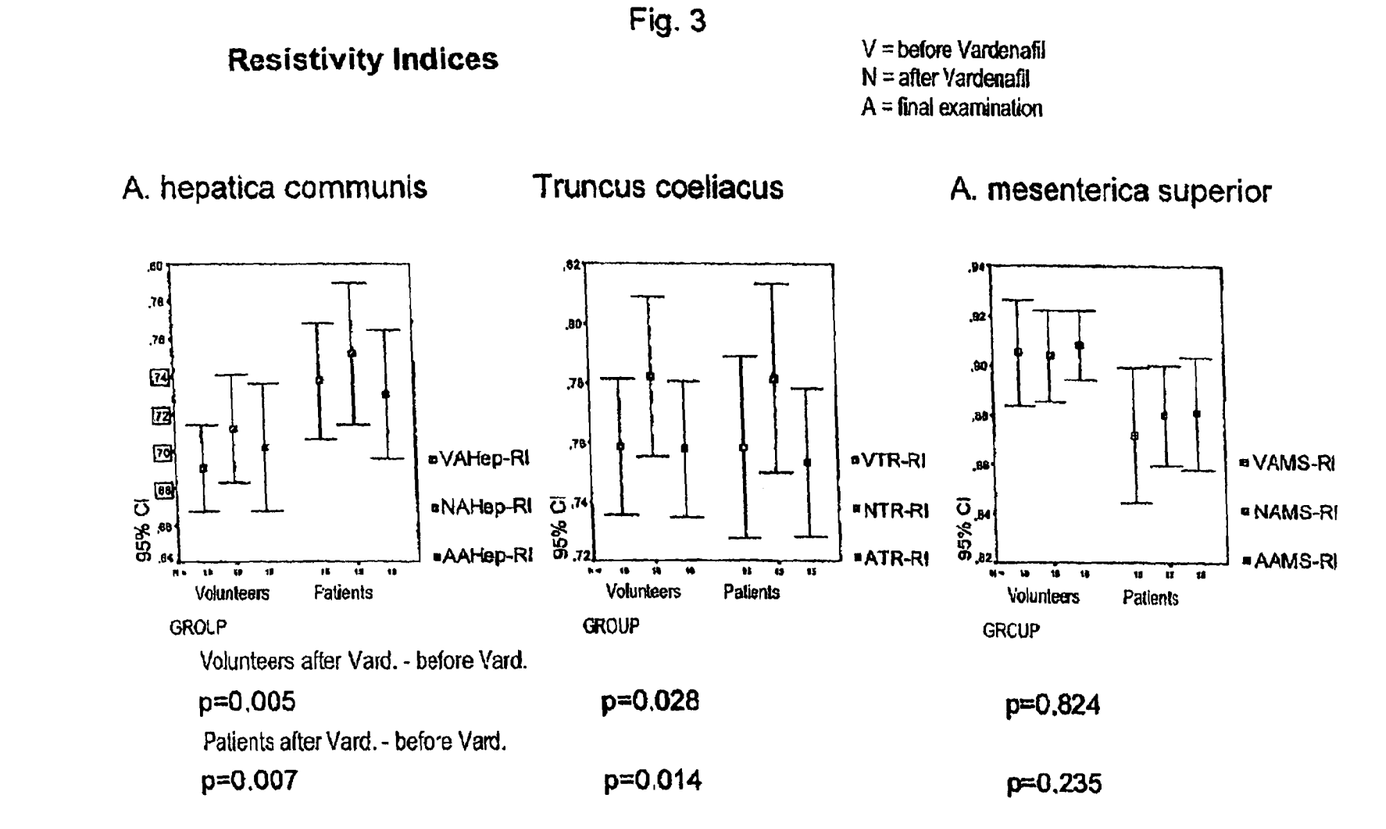
FIG. 3 shows the measurements of arterial blood flow, including Ri-values for A. hepatica and the Truncus coeliacus and A. mesenterica superior, in patients before (V), 1 h after oral administration (N) and in the final examination (A).

Results:

The results of the haemodynamic measurements before (V), 1 h after oral administration (N) and in the final examination (A) are shown in FIGS. 1 to 3. The portal vein diameter slightly increases in the patients (FIG. 1). It remains constant in normal volunteers. By means of the PDE 5-inhibitor, the portal flow surprisingly increases in the volunteers and even more pronounced in the patients in a significant manner (FIG. 2), whilst the arterial blood flow through the liver is not enhanced (FIG. 3); one even sees an increase of the Ri-values for A. hepatica and the Truncus coeliacus. Contrary to that, the Ri-values of the A. mesenterica superior remain unaffected.

Figure 4:
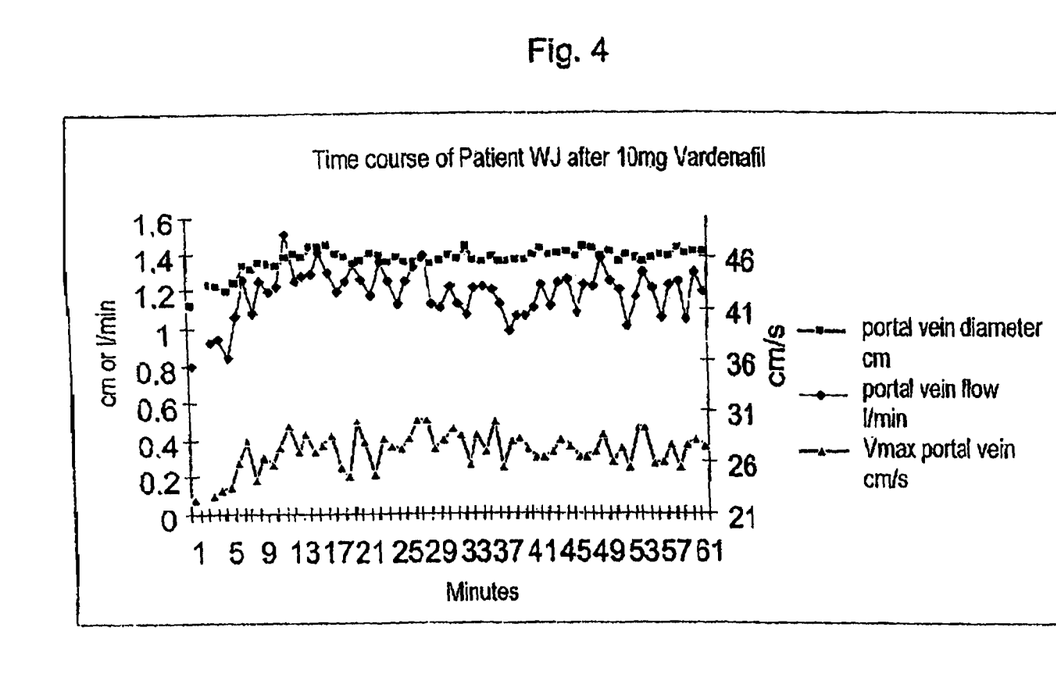
FIG. 4 shows an example of the continuous measurement in an individual patient (cause of portal hypertension: liver cirrhosis) after oral administration of 10 mg Vardenafil.

FIG. 4 shows an example of the continuous measurement in an individual patient (cause of portal hypertension: liver cirrhosis) after oral administration of 10 mg Vardenafil. Similar to practically all other patients, the increase of flow velocity in the portal vein (cm/sec) and above all the portal vein flow (1/min) is clearly detectable already after 15 min. The effect appears to be most pronounced after 20-30 min, while, however, prolonging further for at least one hour.

Example 3

In accordance with the study described in the $2^{nd}$ series of examples, the effects of oral administration of Vardenafil was carried out with two patients, who had a pathological collateral or detour circulation, as originally caused by liver cirrhosis. Hereby, before and after a single oral administration of 10 mg Vardenafil, the flow in the porto-systemic detour circulation was measured by Doppler-sonography: once in a patient having V. coronaria ventriculi as well as oesophagus varices, and another time in a patient having re-opened V. umbilicalis.

As a result, it was found that the total flow in the portal vein increased, whereas the flow in the V. coronaria ventriculi or in the umbilical vein decreased by about 30%. With this result, the extremely preferable effect is demonstrated that, due to the increase of the portal flow while having an invariable arterial inflow, the portal pressure could decrease, and, as a consequence, the detour circulation could be forced back. By the decrease of the flow through the detour circulation, the risk of varice bleedings as well as other complications, diseases or disease conditions being associated with the presence of a detour circulation is lowered.

Example 4

In a patient having liver cirrhosis due to a chronic Hepatitis C, the wedged hepatic vein pressure, which can be equated with the portal vein pressure, was measured invasively. For this, a balloon catheter was introduced through the Vena jugularis interna into a small hepatic vein under X-ray control. Then, the free hepatic vein pressure may be measured, when the tip of the catheter lies freely in the lumen of the small vein. When the balloon is dilated (the diameter of this small hepatic vein amounts to a few mm), a congestion pressure is built-up at the tip of the catheter, corresponding to the portal vein pressure. In the tested patient, the portal vein pressure prior to the oral administration of a medicament was at 31 mm Hg. Already 10 minutes after the administration of 10 mg Vardenafil, it showed a tendency to decrease, and 25 minutes after the administration of the substance, it was at 26 mm Hg.

Thus, it was confirmed by direct pressure measurement that the conclusion from the indirect measurements of the liver haemodynamics are correct: by inhibitors of PDE 5, the portal vein pressure in patients having portal hypertension is decreased.

The invention claimed is:

1. A method for the treatment of portal hypertension in a human having been diagnosed with portal hypertension and with one or more of the following conditions: bleeding complications of the portal hypertension, hepato-renal syndrome, hepato-pulmonal syndrome, hepatic encephalopathy, spontaneous bacterial peritonitis and ascites, the method comprising administering to said human a portal blood flow increasing amount of a compound that inhibits phosphodiesterase type 5 (PDE 5), or of a pharmaceutical composition containing said compound.

2. The method according to claim 1, wherein said human has been diagnosed with bleedings from oesophagus varices and/or fundus varices.

3. The method according to claim 1, wherein the PDE 5-inhibitor is selected froth the group consisting of Sildenafil, Tadalafil and Vardenafil.

4. The method according to claim 3, wherein Vardenafil is selected as the PDE 5-inhibitor.

5. The method according to any one of claim 1 or 4, wherein the PDE 5-inhibitor or the pharmaceutical composition containing a PDE 5-inhibitor is administered orally.

6. The method according to claim 5, wherein the PDE 5-inhibitor is administered orally as a single dose in an amount of 0.01 to 10 mg PDE 5-inhibitor per kg body weight of a human.

7. The method according to claim 1, wherein the effective dose is administered orally as a single dose in an amount of 0.01 to 10 mg per kg body weight of a human.

8. The method according to claim 5, wherein the PDE 5-inhibitor is administered orally as a single dose in an amount of 0.1 to 1.5 mg PDE 5-inhibitor per kg body weight of a human.

* * * * *